United States Patent [19]

Hudrlik

[11] Patent Number: 5,480,441
[45] Date of Patent: Jan. 2, 1996

[54] RATE-RESPONSIVE HEART PACEMAKER

[75] Inventor: Terrence R. Hudrlik, Fridley, Minn.

[73] Assignee: Medtronic, Inc., Minneapolis, Minn.

[21] Appl. No.: 220,757

[22] Filed: Mar. 30, 1994

[51] Int. Cl.$^6$ ........................................ A61N 1/36
[52] U.S. Cl. ........................................ 607/17; 607/9
[58] Field of Search ................... 607/8, 17, 19, 607/20, 28; 128/716

[56] References Cited

U.S. PATENT DOCUMENTS

| | | |
|---|---|---|
| 3,593,718 | 7/1971 | Krasner . |
| 4,576,183 | 3/1986 | Plicchi et al. ............ 607/20 X |
| 4,596,251 | 6/1986 | Plicchi . |
| 4,702,253 | 10/1987 | Nappholz . |
| 4,721,110 | 1/1988 | Lampadivs ................. 607/20 |
| 4,757,815 | 7/1988 | Strandbrg . |
| 4,817,606 | 4/1989 | Lekholm . |
| 4,901,726 | 2/1990 | Hansen . |
| 5,156,149 | 10/1992 | Hudrlik . |
| 5,233,985 | 8/1993 | Hudrlik . |
| 5,243,981 | 9/1993 | Hudrlik ..................... 607/11 |
| 5,265,603 | 11/1993 | Hudrlik . |
| 5,411,529 | 5/1995 | Hudrlik ..................... 607/9 |

FOREIGN PATENT DOCUMENTS

| | | | |
|---|---|---|---|
| 9202274 | 2/1992 | WIPO | ...... 607/17 |
| 9210236 | 6/1992 | WIPO . | |
| 9318821 | 9/1993 | WIPO | ...... 607/17 |

OTHER PUBLICATIONS

Bioelectric Amplifiers, Chapter 4, in: Joseph J. Carr and John M. Brown (eds) Introduction to Biomedical Equipment Tech., John Wiley & Sons: New York 1981 pp. 41–44.

Primary Examiner—William E. Kamm
Assistant Examiner—Jeffrey R. Jastrzab
Attorney, Agent, or Firm—Reed A. Duthler; Harold R. Patton

[57] ABSTRACT

A rate-responsive pacemaker pulse generator and lead system that allows the rate at which the pacemaker delivers electrical stimulation pulses to the heart to be adjusted as needed in order to satisfy the body's physiological needs. The pulse generator and lead system include first and second electrodes coupled to a virtual load and monitoring circuit for monitoring the electrical energy provided through the virtual load in order to detect the magnitude of cardiac depolarization signals. The impedance of the virtual load is intentionally mismatched to the source impedance of the cardiac tissue in order to increase the peak-to-peak variation of the cardiac depolarization signals as a function of modulation of the tissue source by respiratory activity. The peak to peak modulation of the cardiac signals is processed to provide a pacing rate control signal.

9 Claims, 5 Drawing Sheets

RATE-RESPONSIVE HEART PACEMAKER

CROSS-REFERENCED RELATED APPLICATIONS

Attention is drawn to the commonly assigned U.S. Pat. No. 5,156,149, for "Sensor for Detecting Cardiac Depolarizations Particularly Adapted for use in a Cardiac Pacemaker", issued Oct. 20, 1992 in the name of Terrence R. Hudrlik, U.S. Pat. No. 5,265,603, for "Electronic Capture Detection for a Pacer", issued Nov. 30, 1993 and U.S. Pat. No. 5,233,985, for a "Medical Stimulator With Operational Amplifier Output circuit", filed Jul. 15, 1991 in the name of Terrence R. Hudrlik, all three of which are incorporated herein in by reference in their entireties.

BACKGROUND OF THE INVENTION

This invention relates to implantable pacemakers and more particularly to rate-responsive implantable pacemakers that monitor the variation in the respiration or activity of the user.

Early pacemakers comprised a fixed rate stimulation pulse generator that could be reset on demand by sensed a trial and/or ventricular depolarizations. Modem pacemakers include complex stimulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit. More recently, single and dual chamber pacemakers have been developed that respond to physiologic sensors which, with greater or lesser degrees of specificity, sense the body's demand for oxygenated blood and regulate the pacing rate accordingly.

For example, rate responsive pacing systems have been developed and marketed which rely upon the patient's rate of respiration. Such pacemakers are described, for example, in U.S. Pat. No. 3,593,718 and 4,596,251 and have been commercialized by Biotec and Telectronics. These pacemakers use an impedance pneumograph for acquiring a respiration signal. Such an impedance pneumograph requires additional electrodes and a separate signal generator, in most instances, for impedance measurement. More recently, it has been proposed to employ the variation of the peak-to-peak amplitude of the EGM signals as a rate control signal on the premise that the amplitude varies as a function of the patient's activity and/or respiration as disclosed in U.S. Pat. No. 4,757,815.

SUMMARY OF THE INVENTION

It is an object of the present invention to provide a heart pacemaker which varies the pacing rate in dependence upon a variable of the patient's EGM related to respiration. Sensing of the patient's EGM is accomplished through the use of a field density clamp (FDC) amplifier having a virtual load impedance across the sensing electrodes which is purposely mismatched to the body tissue source impedance.

In medical applications, it is conventional that the biological signal amplifiers have very high input impedances. Conventional biological engineering design practices dictate that such an amplifier's input impedance must be at least an order of magnitude higher than the source impedance. See for example, "Bioelectric Amplifiers," in *Introduction to Biomedical Equipment Technology* by Carr and Brown, John Wiley & Sons, 1981, pages 41–44 at 42. In accordance with the present invention, however, the virtual load impedance of the FDC amplifier may be adjusted to be substantially less than the tissue source impedance which, in the case of heart tissue, typically is in the range of 500–1000 ohms.

In contrast to the approach taken by the prior art, the present invention utilizes an FDC sense amplifier which uses active detection circuitry to monitor the amount of current or power delivered through a virtual load across the sensing electrodes as a result of the passage of a cardiac depolarization wave front through the tissue adjacent the electrodes. Maximization of the transfer of power through the virtual load is accomplished by adjusting the virtual load impedance to approximate the tissue source impedance.

It has been found that respiration causes physical changes in the cardiac tissue located adjacent to the probe electrode which modulates the amplitude of the depolarization wave front signal sensed by the amplifier. The amount of this modulation can be deliberately emphasized by selection of a non-optimal power transfer by adjustment of the virtual load impedance.

In a preferred embodiment of the present invention, the invention comprises a pulse generator for generating pacing pulses; first and second electrodes for sensing cardiac signals; a virtual load effectively connected across the electrodes; an active circuit for providing electrical energy to the electrodes through the virtual load in response to the passage of a cardiac polarization wave front; monitoring circuitry for monitoring electrical energy provided through the virtual load, for detecting the occurrence of cardiac depolarizations and for monitoring the amplitude fluctuations thereof which vary according to respiratory activity of the pacemaker user; and control circuitry for changing the rate of pacing pulses generated by the pulse generator in response to the respiratory activity of the patient.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

In the following description, reference is made to an illustrative embodiment for carrying out the invention. It is understood that other embodiments may be utilized without departing from the scope of the invention.

Figure 1:
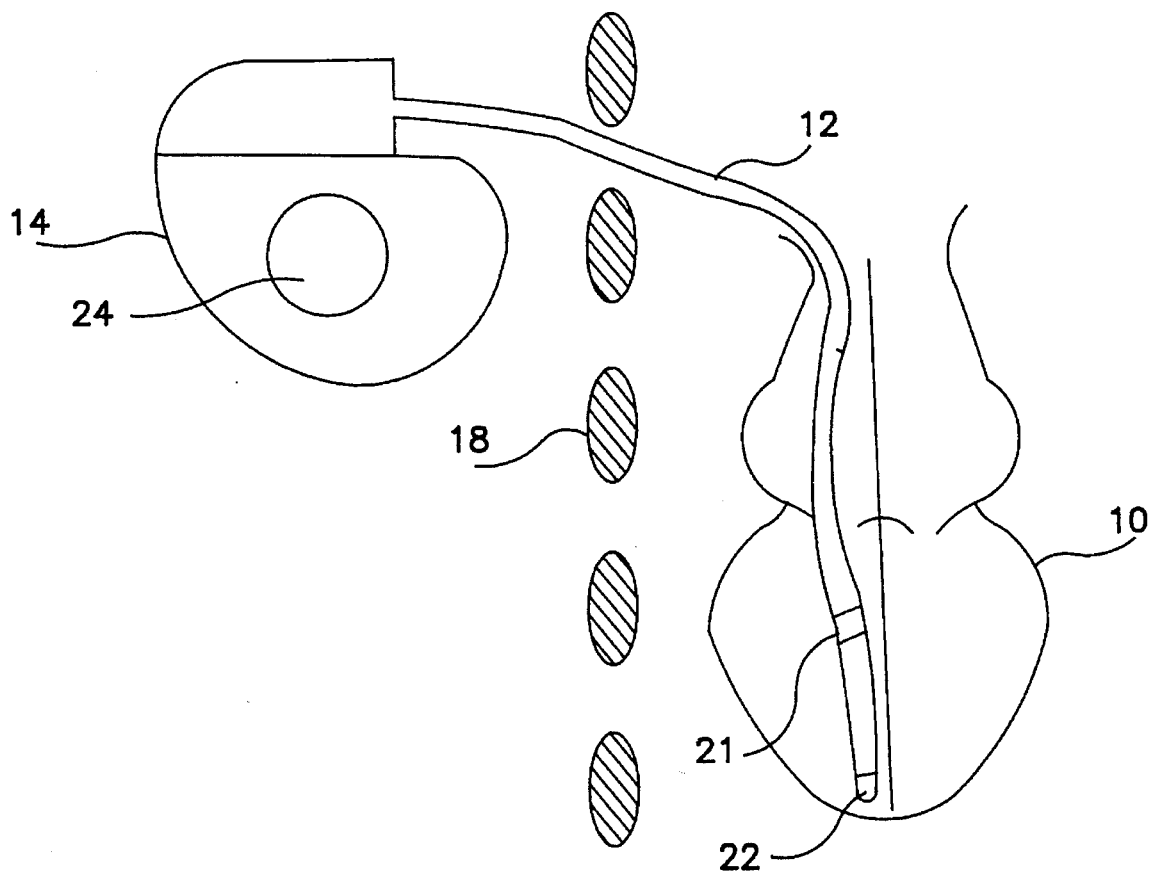
FIG. 1 is a diagram depicting the interconnection between a pacer according to the present invention and the heart.
Figure 1:
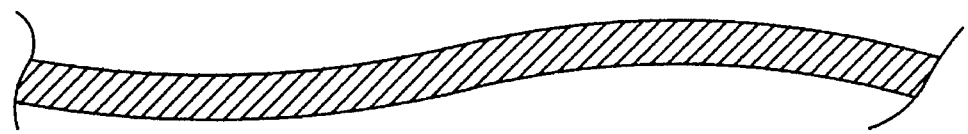

FIG. 1 is a schematic diagram depicting the interconnection between the pacer and the heart. For purposes of illustration, a composite unipolar/bipolar ventricular inhibited pacer is shown with a lead bearing two electrodes situated in the ventricle.

Typically, the pacemaker 14 is implanted beneath the skin, outside the rib-cage 18. A pacing lead 12 is passed pervenously into the right ventricle of the heart 10. The pacing lead 12 is used for supplying pacing pulses to the heart and for conducting electrical signals resulting from the depolarization of the heart to the pacemaker 14. There am two basic electrical configurations for pacing leads. A unipolar electrode system would include tip electrode 22 referenced to a can or case electrode 24. In a bipolar lead system, a ring electrode 21 is included on the lead 12. In the bipolar mode, this ring electrode may be used as the reference electrode for either sensing or pacing. In both cases, the electrode in direct contact with cardiac tissue is the tip electrode 22 which is referred to herein as the "probe" electrode.

In unipolar application, the implanted pacer is implanted subcutaneously in the right chest, outside of the ribs 18. This configuration places at least the tip electrode 22 within the heart, and the case electrode 24 outside of the heart, with the syncytium of the heart located between the electrode poles. Typically, the distance between the distal tip electrode 22 and the pacer can electrode 24 is between 10 and 30 cm.

In bipolar applications, the case electrode 24 is not used and the tip and proximal ring electrodes 22 and 21 are connected to the pacemaker pulse generator output circuit and sense amplifiers. Typically, the tip and ring electrodes 22 and 21 are spaced apart between 0.5 and 3.0 cm. In dual chamber pacemakers, unipolar and/or bipolar electrodes are similarly situated in or on the atrium or coronary sinus.

The preferred embodiment of the present invention may be practiced with conventional pacing leads and electrodes. The field density clamp may, however, advantageously be used with electrodes of smaller than conventional surface area. The electrode surface areas of the first and second spaced bipolar electrodes are preferably in the range of 0.25 mm$^2$ to 5.0 mm$^2$, preferably less than 1.0 mm$^2$.

Figure 2:
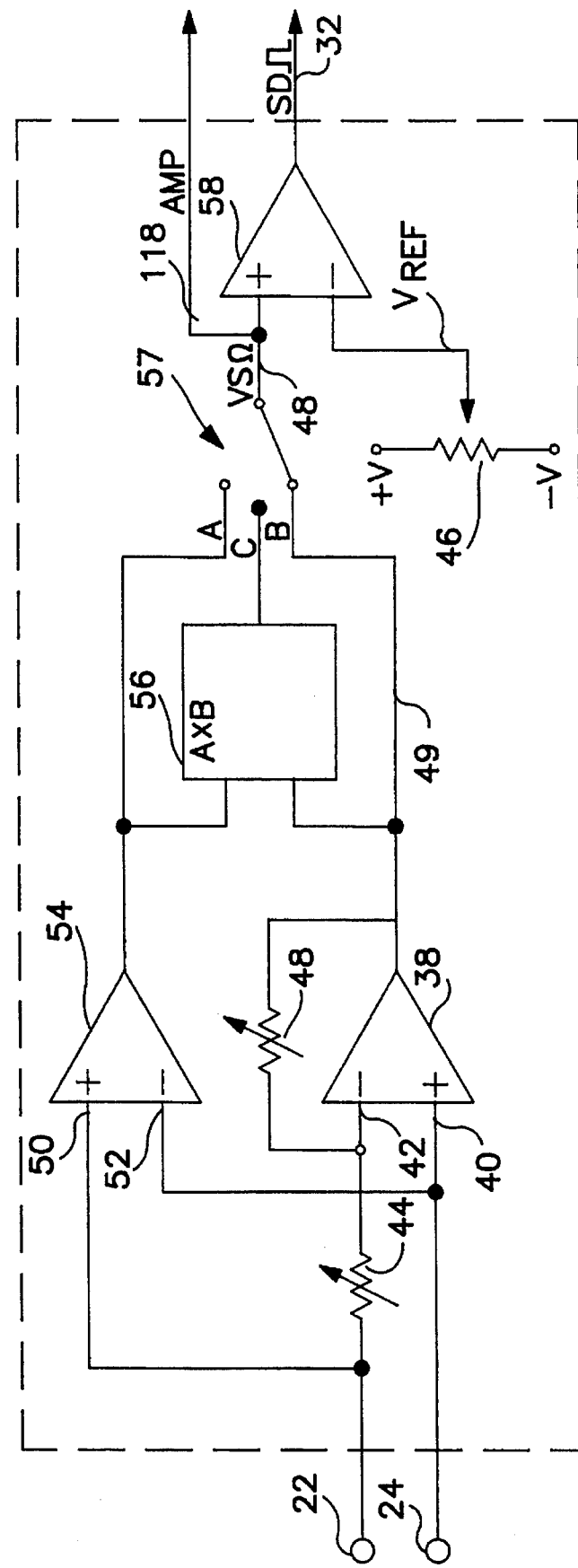
FIG. 2 is a schematic diagram of an FDC sense amplifier circuit for use in carrying out the invention.

FIG. 2 discloses an FDC amplifier for use in conjunction with the present invention. This form of amplifier is also described in the above-cited co-pending patent applications by Hudrlik, incorporated by reference in their entirety. The active circuitry, comprising operational amplifier 38, attempts to maintain equal voltage levels at its two inputs. Passage of a depolarization wavefront changes the distribution of electrical charges in the vicinity of the probe electrode 22. This disturbance results in the active circuitry of the operational amplifier 38 delivering electrical current through feedback resistor 48 and virtual load resistor 44 to maintain equal voltages at its inputs. This current, delivered to probe electrode 22, serves both to reestablish the equilibrium condition in effect preceding the passage of the depolarization wavefront and to signal the occurrence of the depolarization wavefront.

As shown in the schematic diagram of FIG. 2, the sense amplifier may be practiced with an operational amplifier 38 which has its non-inverting input 40 connected to the can electrode 24. The inverting input 42 is coupled to tip electrode 22 through a variable resistor 44 which is used to set a virtual load resistance for the system. This resistance is preferably between 10 and 1000 ohms, and may be less than 100 ohms for use in conjunction with small surface area electrodes, typically about 5 square millimeters or less in surface area.

The inventor has determined that when an amplifier according to the present invention is coupled to a canine heart by means of a polished platinum probe electrode, R-waves exhibited during normal sinus rhythm place a peak demand for current through the virtual load of about 0.5 microamps per square millimeter of electrode surface. It is preferred that the peak current demand fall in the vicinity of 2.5 microamps or less, which can be accomplished with a platinum electrodes of about 2–5 square millimeters in surface area. Electrodes fabricated of other metals will have differing current requirements and therefore will have differing optimal size ranges. Electrodes directly in contact with the myocardium will typically produce a greater peak current per square millimeter of surface area and therefore will typically have somewhat smaller optimal surface areas.

A feedback path is provided for the amplifier 38 by a feedback resistor 48 which defines a voltage signal B on line 39 proportional to the current through the virtual load 44 and feedback resistor 48. A differential amplifier 54 may optionally be provided to measure the magnitude of the potential difference between electrodes 22 and 25, and thus the voltage across the virtual load 44. The non-inverting input 50 of this differential amplifier 54 is shown coupled to tip electrode 22 while the can electrode 24 is shown coupled to inverting input 52. The voltage signal A output from differential amplifier 54 is proportional to the voltage across the virtual load resistor 44.

The voltage measurement A and the current measurement B may be used to compute the power delivered through the virtual load as a result of the passage of a cardiac depolarization wavefront, if desired. Detection of the passage of the depolarization wavefront based on measured power delivered through the virtual load may be employed for sensing purposes in the context of the present invention. However it is also workable to use the current signal B, alone, to detect cardiac depolarizations.

The power computation, if employed, is carried out by an analog multiplier 56 which computes the power level an provides a voltage output C proportional to the computed power. Current signal B or power signal C is communicated to comparator 58 via switch 57. Comparator 58 compares the selected input to a threshold voltage VREF defined by voltage source 46. If the selected one of the current signal B or the power signal C exceeds Vref, comparator 58 generates a V-sense detect signal VSD on line 32. The selected one of current signal B or power signal C is also provided on AMP line 118 for use in measuring the amplitude variations of detected cardiac depolarizations to derive a measurement of respiration activity.

Figure 3:
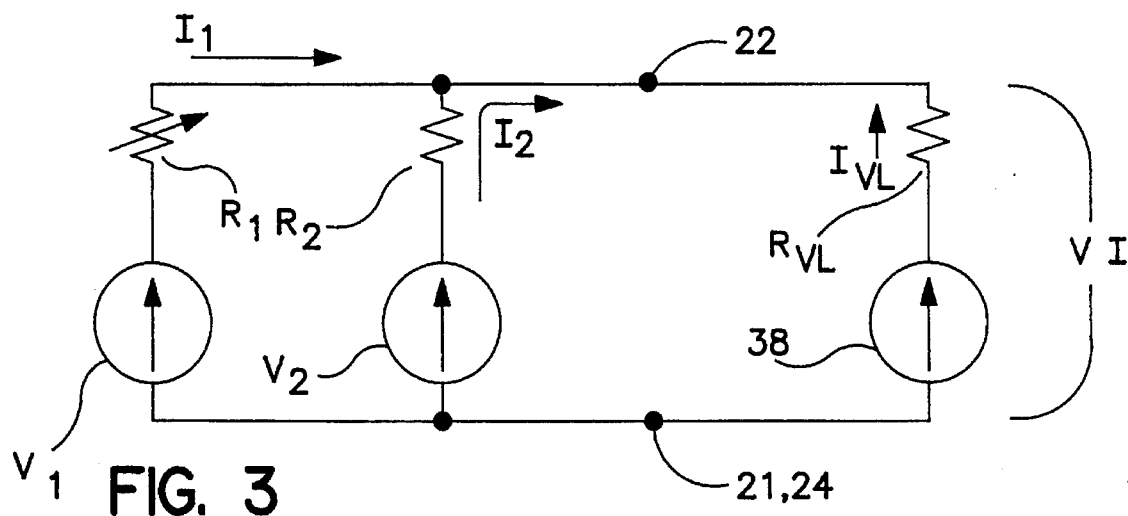
FIG. 3 is an equivalent circuit illustrating the source impedance contributions of far field respiration to the near field cardiac tissue source impedance.

Turning now to FIG. 3, it depicts a simplified Thevenin equivalent diagram of the composite cardiac depolarization wave front and the myoelectric and/or respiration signal generators which operate through a composite source impedance to present a composite signal to the field density clamp sense amplifier and virtual load $R_{v1}$. In FIG. 3, the myoelectric or respiration signal source and variable source impedance are represented by elements $V_1$ and $R_1$, respectively. The cardiac depolarization wave signal generator and source impedance are represented by elements $V_2$ and $R_2$ coupled in parallel with elements $V_1$ and $R_1$. The composite signal is a current $I_1+I_2$ applied to the virtual load $R_{v1}$ across which a power measurement $V_1$ is developed as a function of the amount of power it takes to equalize the potentials across electrodes 22 and 21 or 24. In the context of the present invention, the field density clamp amplifier thus operates as the source of electrical energy applied to the probe and return electrodes to counteract depolarization induced variations in the relative electrical potentials at the first and second electrodes.

Traditional pacing sense amplifier circuits have endeavored to detect only the signal contribution of the cardiac depolarization wave front and to suppress or ignore amplitude variations of the ECG signal caused by artifacts, including respiration and muscle noise or myoelectric disturbances. Traditionally, sense amplifier circuits having high input impedance on the order of 50–100 k ohms have been employed and considerable effort has been expended in lowering the tissue-electrode interface impedance for sensing purposes. The value of $R_2$, that is the cardiac tissue impedance, is generally characterized as between 500 and 1000 ohms. The ten to one mismatch between source impedance and input impedance in the prior art has been employed to suppress signals other than the deflections of the electrogram.

In accordance with the present invention, it has been realized that the maximum power is transferred from a power source to a load when that load is "tuned" or set to the Thevenin equivalent resistance of the power source (tissue source impedance). Since the power source depicted in FIG. 3 is actually two separate power sources with two separate source impedances, and moreover, since the impedance value $R_1$ varies as the patient exhales and inhales, it may be realized that the overall amplitude of the signal across the electrodes varies as a function of the variation in the source impedance $R_1$. For example, the contribution of the source impedance $R_1$ with inhalation and exhalation may in some patients cause the aggregate source impedance to vary between about 525 and 625 ohms. That variation, in relation to the approximately 50–100 k ohm input impedance of conventional pacemaker sense amplifiers is virtually undetectable.

Figure 4:
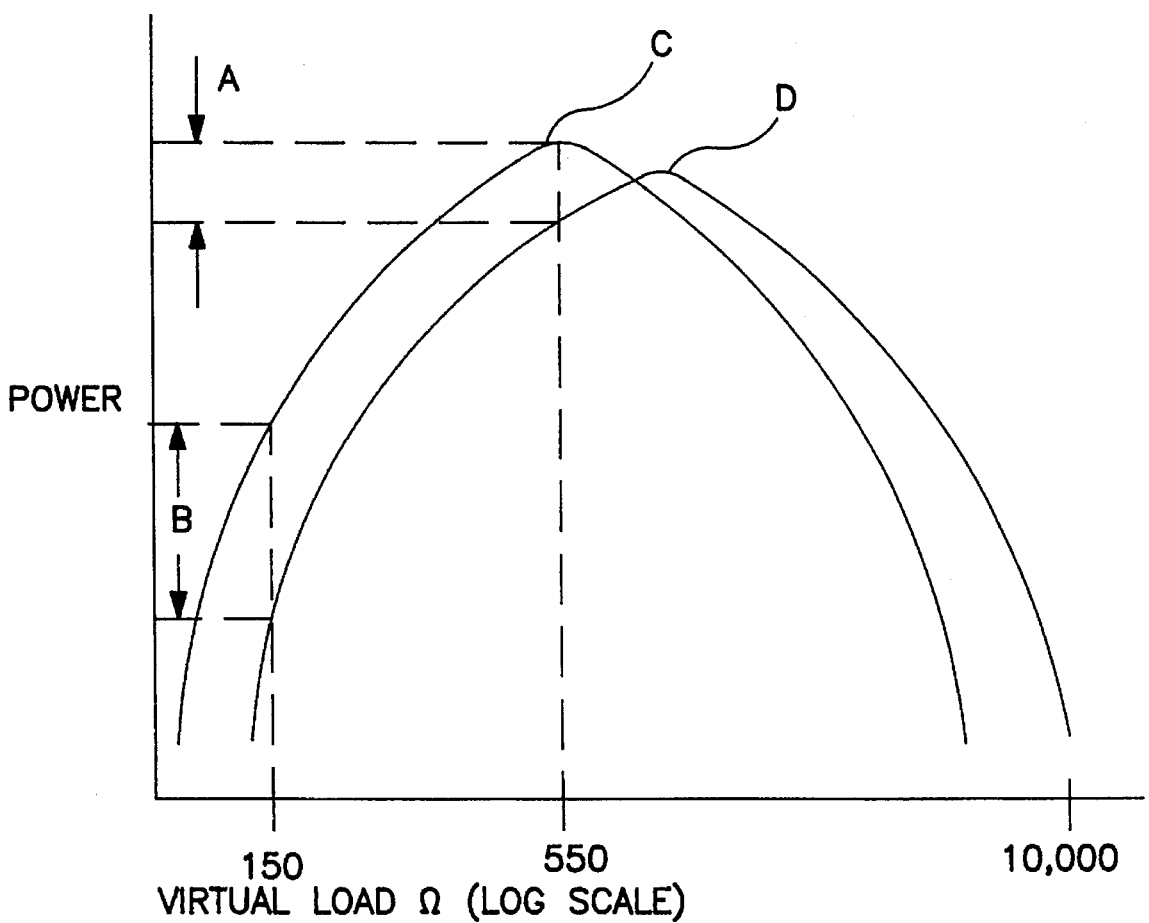
FIG. 4 is a graphical depiction of the effect of varying the virtual load impedance on the ability to detect peak-to-peak EGM amplitude variation due to far field effects on source impedance.

Turning to FIG. 4, the composite power output curves of the two current generators represented by the elements $V_1$, $R_1$ and $V_2$, $R_2$ of FIG. 3 during inhalation (curve D) and exhalation (curve C) are depicted in relation to the virtual load resistance $R_{v1}$, as displayed along a logarithmic scale. Based on testing by the inventor, the power output curves based upon the aggregate source impedance $R_S$ ($R_1$ and $R_2$) are depicted as curves which generally develop about 200 nanowatts power when the virtual load resistance is set in the vicinity of 550 ohms, which nearly matches the source resistances during exhalation and inhalation.

FIG. 4 illustrates that if the virtual load resistance $R_{v1}$ is chosen to approximate the tissue source resistance to produce the peak amplitude power output signal, the difference in measured amplitude from inhalation to exhalation represented by the letter "A" is relatively small, whereas if the virtual load resistance $R_{v1}$ is selected to be about 150 ohms, the difference signal "B" increased by a substantial factor. Putting it another way, if the load resistance is tuned for maximum power transfer, the respiration induced variability in the power transferred per QRS complex is quite small. If the virtual load impedance is tuned away from the point of maximum power transfer, the resultant change in signal power may be made substantially larger.

Figure 5:
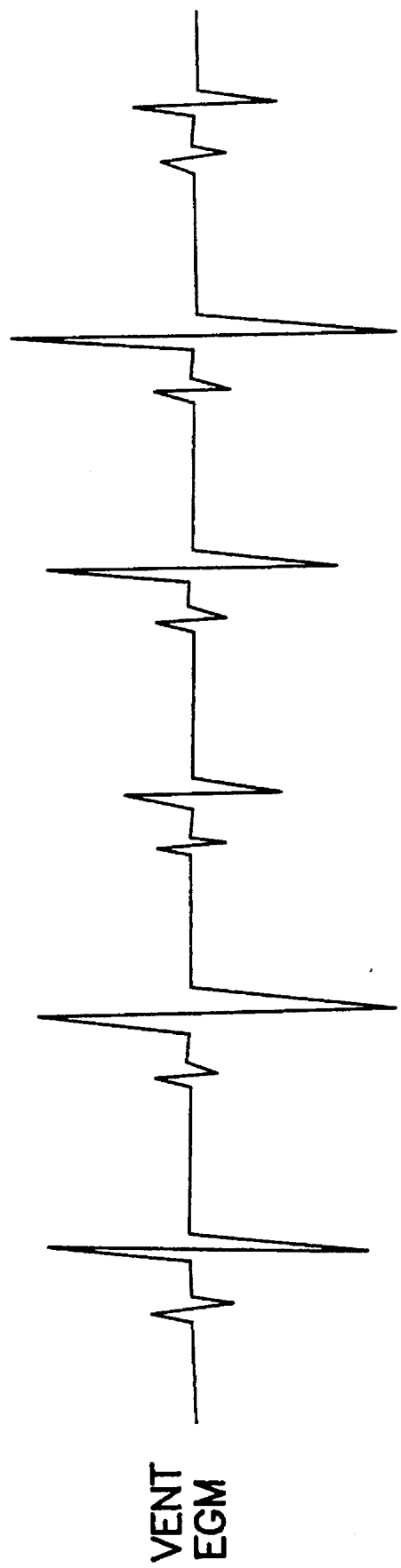
FIG. 5 is a simulated intracardiac EGM tracing of a sequence of QRS complexes varying in amplitude with respiration.

FIG. 5 illustrates simulated EGM tracings based on tracings taken using an FDC sense amplifier with a low virtual load impedance (less than 150 ohms) and a canine model. The tracing illustrates the peak-to-peak amplitude variation in the QRS complex due to respiration. By selecting the virtual load impedance properly as discussed above, it is possible to increase the peak to peak amplitude variation, increasing the ability of the system to respond appropriately to varying levels of exercise without losing the ability to reliably detect the occurrence of cardiac depolarizations.

Figure 6:
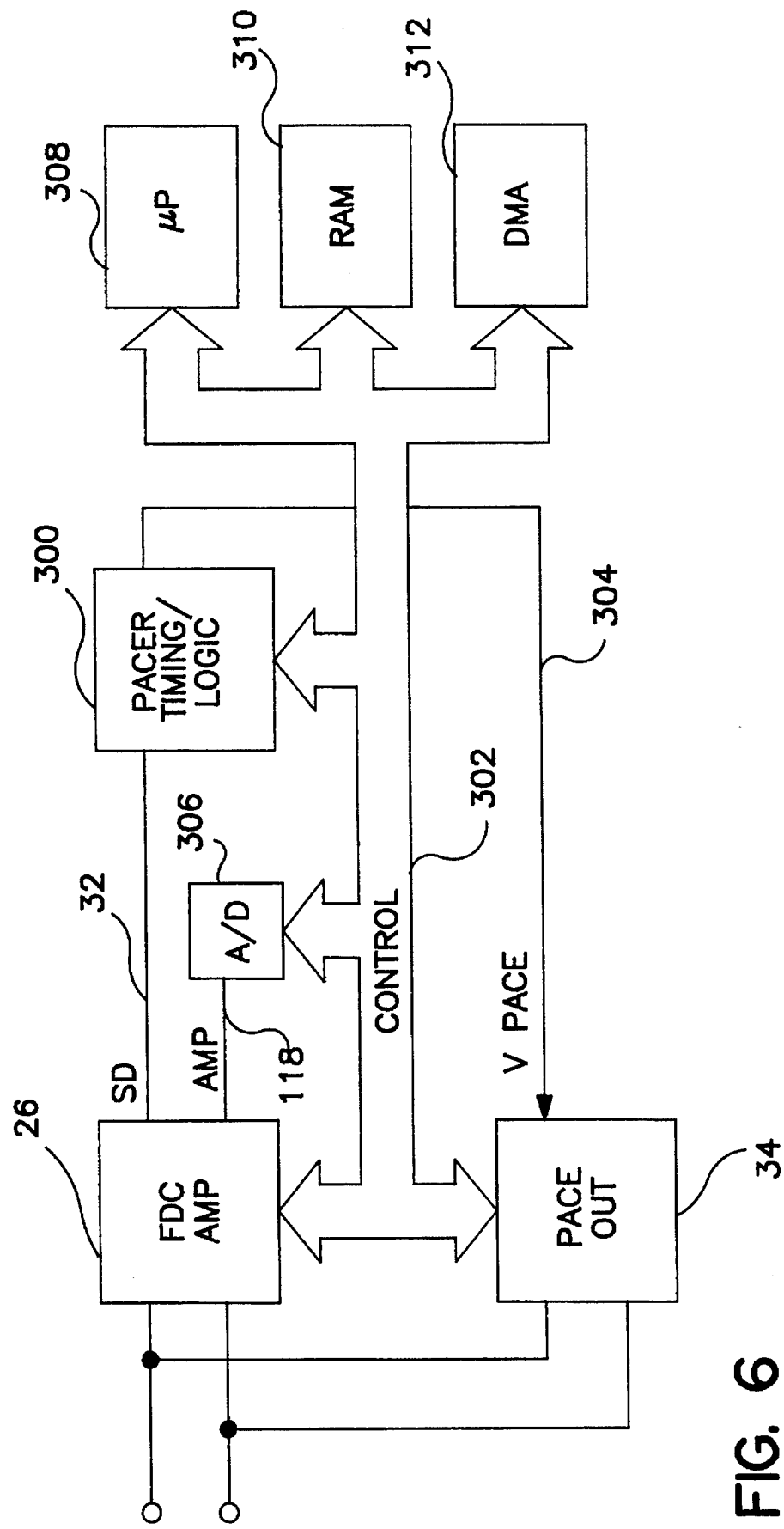
FIG. 6 is a block diagram depicting how the sense amplifier of FIG. 2 may be introduced into a microprocessor controlled, rate responsive pacemaker to embody the present invention.

FIG. 6 is a block diagram of a microprocessor based pacemaker employing the present invention. Operation of the field density clamp amplifier 26 in conjunction with electrodes 22 and 21/24 corresponds to the operation of the same components discussed above in conjunction with FIG. 2. Amplifier 26 provides a sense detect signal on line 32 which is provided to the pacer timing and logic circuitry 300. The analog signal from the operational amplifier within FDC amp 26 is provided on AMP line 118 to an analog to digital converter 306, for storage and waveform analysis. Pacer timing and logic circuitry 300 includes programmable digital counters and associated logic for controlling the intervals conventionally associated with demand cardiac pacing functions. Most importantly, pacer timing logic 300 includes the escape interval timer, the pulse width timer and the any refractory and blanking period timers. The particular intervals timed by pacer timer logic 300 are controlled by microprocessor 308 via address/data bus 302. In response to detection of a depolarization wavefront as indicated by a logic signal on SD line 32, pacer timing logic 300 resets the pacing escape interval timer therein, and initiates any other timing functions that may be desired, under control of microprocessor 308. On expiration of the ventricular escape interval, a trigger signal is generated on line 304 which triggers pacing pulse generator 34 to deliver a pacing pulse of a width defined by microprocessor 308 via address/data buss 302.

The analog output from amplifier 26 is provided to an A-D converter 306, which operates under control of microprocessor 308 via address/data bus 302. This structure allows for storage of the output from amplifier 26 during and following generation of stimulus pulses, and in response to detection of spontaneous or induced cardiac depolarizations. For example, a portion of random access memory 310 may be configured as a recirculating buffer, with the digitized output of amplifier 26 stored therein under control of direct memory access circuitry 312. For example, the previous 100 milliseconds of digitized signal may be present in the recirculating buffer at all times. In response to either delivery of a stimulation pulse or sensing of a depolarization wavefront, microprocessor 308 may freeze the recirculating buffer memory 100 milliseconds thereafter, and transfer the contents of the buffer to a separate location within memory 310 for later analysis. In this fashion, the waveform of the signal on line 118 corresponding delivered stimulus pulse, the waveform corresponding to the operation of the amplifier 26 to restore the electrode-tissue system to its previous equilibrium state and the induced or spontaneous depolarization waveforms may all be retained for analysis.

For purposes of measuring respiratory activity of the patient, it is envisioned that for each stored electrogram segment, a measurement of the maximum peak to peak variation in amplitude will correspondingly be derived and stored. These peak to peak amplitude measurements may be processed in a fashion to that disclosed in U.S. Pat. No. 4,596,251, issued to Plicchi and Canducci, incorporated herein by reference in its entirety. In this patent, the output of an impedance pneumograph is applied to input of a delta modulator circuit which operates to effectively produce a running sum of the measurement to measurement variability of the output of the impedance pneumograph, over a predetermined time interval. In other words, each measurement is compared to the measurement immediately previous thereto, and the absolute value of the derived difference is stored. A running sum of the stored absolute values over a preceding period of time is calculated and is updated every few seconds to derive a measurement of respiratory activity corresponding to minute ventilation.

This measurement of respiratory activity may be employed to regulate pacing rate by the expedient of providing two such running sums of the derived differences. The first sum, which may for convenience be referred to as the "short term value" and may, for example, comprise the sum of the derived differences over the preceding 16 to 32 seconds. The second sum which may for convenience be referred to as the "long term value" may, for example, reflect the sum of the derived differences over the preceding 16–32 minutes. The difference between the short term value and the long term value may be used as a measurement of respiratory activity, and used to regulate the ventricular pacing rate. For example, a similar system employing comparison of short term and long term values of respiratory activity is disclosed in U.S. Pat. No. 4,702,253, issued to Nappholz et al., also incorporated herein by reference. The Nappholz patent also discloses the use of an impedance pneumograph to derive the initial measurements which are processed to derive the short and long term values. The Nappholz patent is believed generally to correspond to the Meta-MV (registered trademark) pacemaker marketed by Telectronics, Inc. As such, processing the measured amplitudes of the stored electrogram signals to produce a measurement of respiratory activity is believed to be well within the skill of the art, using methods and algorithms disclosed in the above cited Plicci and Canducci and Nappholtz patents or other methods.

It is also contemplated that the present invention may be practiced in the context of a pacemaker which is capable of automatic adjustment of the FDC sense amplifier virtual load impedance. For example, the impedance may be adjusted by the physician by means of an external programmer or automatically by the pacemaker, during exercise, in order to produce a measured variability in the peak to peak QRS amplitudes that falls within predetermined values. It is also envisioned that the pacemaker may update and readjust the value of the virtual load impedance based upon actual measured QRS amplitude variability during respiration.

For example, an adjustment system corresponding to that disclosed in U.S. Pat. No. 4,901,726, issued to Hansen, also incorporated herein by reference in its entirety may be employed. The Hansen patent discloses a system for updating the gain setting of a physiologic sensor by comparing the output of the sensor, over an extended time period, to a preset expected profile of sensor outputs, and adjusting the sensor gain automatically in order to produce an actual sensor output profile which matches the expected profile. In a similar fashion, the QRS amplitude variability in a pacemaker according to the present invention may be monitored in order to determine how often the measured QRS amplitude differences meet certain predetermined thresholds, and the virtual load impedance adjusted in automatically in response thereto in order to minimize the difference between the actual measured QRS amplitude variability and the expected QRS amplitude variability. Other forms of automatization and optimization are also believed workable in conjunction with the present invention.

Although an exemplary embodiment of the present invention has been shown and described, it will be apparent to those of skill in the art that a number of changes, modifications, or alterations to the invention as described herein may be made, none of which depart from the spirit of the present invention. All such changes, modifications and alterations should therefore be seen within the scope of the present invention.

For example, while the invention has been specifically disclosed in the context of a pacemaker adapted to measure the variability in QRS complex amplitude using an FDC amplifier, the inventors have also determined that a similar variation in P-wave amplitude may also be detected, from the atrium. Thus, while the system as disclosed is directed a pacemaker which senses and paces in the ventricle, an alternative workable embodiment would include the same sort of device, but with the probe electrode located in the atrium. In addition, in such a device, additional ventricular electrodes might also be provided in allow for dual chamber pacing in any known pacing mode.

Further, while the embodiment disclosed is specifically directed to the use of the FDC sense amplifier to detect respiration induced variation of the source impedance of the body tissue in the vicinity of the sensing electrodes, it should be considered within the scope of the invention to use the ability to enhance impedance related variability of the sensed EGM to detect other phenomena and/or to use other features of the sensed EGM signals to regulate the functioning of the pacemaker.

In addition, while the disclosed embodiment takes the form a microprocessor based implementation, this implementation is intended to be merely exemplary. The invention could as well be practiced by the use of a full custom integrated digital circuit or by means of circuitry employing analog timing, processing and memory capabilities. As such, the above disclosure should be considered exemplary, rather than limiting with regard to the following claims.

What is claimed is:

1. A rate-responsive cardiac pacemaker for implantation in a patient, comprising:

pulse generator means for generating pacing pulses at a defined pacing rate;

means for applying said pacing pulses to the heart;

first and second electrode means for sensing cardiac depolarization wave fronts passing in the vicinity of said first electrode means;

virtual load means coupled to said first electrode means for providing a load impedance less than an effective tissue source impedance presented to said first and second electrode means;

active circuit means, coupled to said virtual load means for providing electrical energy to said first electrode means through said virtual load means in response to passage of a cardiac depolarization wave front to counteract depolarization induced variation in relative electrode potentials of said first and second electrode means;

monitoring means, coupled to said active circuit means, for monitoring electrical energy provided through said virtual load means, comprising means for detecting occurrences of cardiac depolarizations and providing cardiac depolarization output signals having a characteristic which varies according to activity level of the patient;

signal measuring means for measuring variations of said characteristic and for generating a control signal therefrom representative of the level of activity of said patient; and control means coupled to said pulse generator means and to said signal measuring means for changing the defined pacing rate of pacing pulses generated by said pulse generator means in response to said control signal.

2. A rate-responsive cardiac pacemaker according to claim 1, wherein said signal measuring means comprises means for measuring variations in amplitude of said cardiac depolarization output signals.

3. A rate-responsive cardiac pacemaker according to claim 2, wherein said signal measuring means comprises means for detecting cumulative variations of peak amplitudes of said of said cardiac depolarization output signals over a predetermined period of time.

4. A rate-responsive cardiac pacemaker according to claim 1, wherein said signal measuring means comprises means for deriving a measurement of respiratory activity based on said characteristic.

5. A rate-responsive cardiac pacemaker according to claim 1, wherein said virtual load means comprises means for providing a load impedance of about 150 ohms or less.

6. Apparatus for measuring respiratory activity of a patient, comprising:

first and second electrode means for sensing cardiac depolarization wave front signals passing in the vicinity of said first electrode means;

virtual load means coupled to said first electrode means for providing a load impedance less than an effective tissue source impedance presented to said first and second electrodes;

active circuit means, coupled to said virtual load means for providing electrical energy to said first electrode means through said virtual load means in response to passage of a cardiac depolarization wave front to counteract depolarization induced variation in relative electrode potentials of said first and second electrode means;

monitoring means, coupled to said active circuit means, for monitoring electrical energy provided through said virtual load means, comprising means for detecting occurrences of cardiac depolarizations and providing cardiac depolarization output signals having a characteristic which varies according to respiratory activity; and signal measuring means for measuring variations of said characteristic and for generating a signal therefrom representative of respiration activity.

7. Apparatus to claim 6, wherein said signal measuring means comprises means for measuring variations in amplitude of said cardiac depolarization output signals.

8. Apparatus according to claim 7, wherein said signal measuring means comprises means for detecting cumulative variations of peak amplitudes of said of said cardiac depolarization output signals over a predetermined period of time.

9. Apparatus according to claim 6, wherein said virtual load means comprises means for providing a load impedance of about 150 ohms or less.

* * * * *